(12) United States Patent
Wang et al.

(10) Patent No.: US 8,780,348 B2
(45) Date of Patent: Jul. 15, 2014

(54) APPARATUS FOR QUANTIFYING UNKNOWN STRESS AND RESIDUAL STRESS OF A MATERIAL AND METHOD THEREOF

(71) Applicant: National Tsing Hua University, Hsinchu (TW)

(72) Inventors: Wei-Chung Wang, Hsinchu (TW); Chi-Hung Huang, Hsinchu (TW); Po-Chi Sung, Hsinchu (TW); Wei-Ren Chen, Hsinchu (TW); Guan-Ting Lai, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 3 days.

(21) Appl. No.: 13/622,358

(22) Filed: Sep. 18, 2012

(65) Prior Publication Data

US 2013/0250277 A1   Sep. 26, 2013

(30) Foreign Application Priority Data

Mar. 16, 2012 (TW) .............................. 101109034 A

(51) Int. Cl.
*G01J 4/00* (2006.01)
*G01L 1/24* (2006.01)
*G01N 21/23* (2006.01)

(52) U.S. Cl.
CPC . *G01L 1/24* (2013.01); *G01L 1/241* (2013.01); *G01N 21/23* (2013.01)

USPC .............................................. 356/364; 356/33

(58) Field of Classification Search
CPC ........................................................ G01N 4/00
USPC ............................................ 356/33, 364, 365
See application file for complete search history.

(56) References Cited

U.S. PATENT DOCUMENTS

| 5,400,131 | A | 3/1995 | Stockley et al. |
| 6,975,397 | B2 * | 12/2005 | Hug ............................. 356/364 |
| 8,264,675 | B1 * | 9/2012 | Danyluk et al. ................. 356/33 |
| 8,537,342 | B2 * | 9/2013 | Danyluk et al. ................. 356/33 |
| 2006/0141466 | A1 * | 6/2006 | Pinet et al. ......................... 435/6 |
| 2006/0238759 | A1 * | 10/2006 | Okabe et al. .................. 356/369 |
| 2006/0256334 | A1 * | 11/2006 | Hug .............................. 356/364 |
| 2012/0314202 | A1 * | 12/2012 | Danyluk et al. ................. 356/33 |

* cited by examiner

*Primary Examiner* — Roy M Punnoose
(74) *Attorney, Agent, or Firm* — Rabin & Berdo P.C.

(57) ABSTRACT

An apparatus for quantifying unknown stress and residual stress of a material to be tested, the material being a birefringent or temporary birefringent material, which includes a light source, a polarizer in front of the light source for converting a light beam from the light source into a beam with linear polarization, a first quarter-wave plate in front of the polarizer for generating circular polarization, a standard material, a second quarter-wave plate, an analyzer, a loading unit, a spectrometer for obtaining transmissivity spectrum of the standard material under the wavelength of the light source and a detecting module connected to the spectrometer to have the transmissivity spectrum of the material to be tested and consequently a stress quantifying formula for the standard material.

7 Claims, 10 Drawing Sheets

ABSTRACT / US 8,780,348 B2

APPARATUS FOR QUANTIFYING UNKNOWN STRESS AND RESIDUAL STRESS OF A MATERIAL AND METHOD THEREOF

CROSS-REFERENCE TO RELATED APPLICATION

This application claims priority from application No. 101109034, filed on Mar. 16, 2012 in the Taiwan Intellectual Property Office.

FIELD OF THE INVENTION

The invention relates to an apparatus for quantifying unknown stress and residual stress of a material, and more particularly, to an apparatus for quantifying the unknown and residual stress of a material by using a polarizer in front of a light source, a first and a second quarter-wave plates to convert light beam into beams with circular polarization and/or linear polarization. respectively. A method for quantifying the unknown and residual stress of a material is also disclosed.

BACKGROUND OF THE INVENTION

Thin Film Transistor-Liquid Crystal Display (TFT-LCD) is one of the promising industries nowadays. The technology for manufacturing displays has been advanced with an unimaginable speed. However, during the race between technology advancement and consumers' pursuit of higher visual satisfaction, a major problem, MURA, pixel defects or wide-area pixel defects (also known as Mura defects), surfaces itself and bothers the manufacturers a great deal. There are a lot of reasons for causing the Mura defects. The reasons are generally classified into two categories; the cell unit defects and the backlight unit defects. Still, the residual stress remained in the glass substrate is also one of the reasons that the manufacturers cannot overlook. As a result of this, measurement of the residual stress has also become important.

Photoelasticity is a real-time, full-field, high sensitive and non-destructive stress measurement method. Mainly, it uses the birefringent material at issue or the temporary birefringent material at issue to examine the residual stress remained in the material at issue. The former employs the characteristics of the difference between the refraction index of the direction of the optical axis of the material at issue and the refraction index of the direction of the orthogonal optical axis. Yet, the latter uses the birefringent feature of the material at issue under a stress.

U.S. Pat. No. 5,400,131 discloses a method for measuring stress in an object of birefringent materials. The stress has both magnitude and direction. The method comprises steps of passing polarized light of first, second and third wavelengths through an object and an analyzer to produce respective fringe patterns, measuring and recording intensities of light for each wavelength emitted from the analyzer for multiple positions in the respective fringe patterns and combining the recorded intensities for the first, second and third wavelengths to form a ramp map having discontinuities at predetermined values of stress and converting the ramp map to a stress map indicating the magnitude of the stress in the object as a function of position within the object, which cannot quantify residual stress precisely because each predetermined value comes from a different source.

In the conventional photoelastic method, the stress-optic law, by analyzing light intensity and extracting the fringe order of isochromatic fringe pattern, is followed when used in quantifying the material stress. Then from the predetermined or known stress-optic coefficient or known wavelength of a light source, the material stress value is then calculated. As introduced, the quantifying method for measuring material stress has to use different measurement systems to acquire stress-optic coefficient and wavelength, which will lead to accumulation of errors from different systems and is not appropriate for quantifying material stress which requires precise measurement. In addition, those required stress-optic coefficient and wavelength may not be independent from each other such that when the material stress value is low, i.e., unknown stress and/or residual stress, the final calculation of the stress will not be correct and is not appropriate for measuring material stress. In addition, the conventional photoelasticity often uses full-field image acquisition equipment and that is not available to present different light intensities from different wavelengths of light.

Furthermore, in the conventional stress measurement method, a comparison between spectrum of the known stress in the database and spectrum of an unknown stress is conducted. Once there is a match, the unknown stress then becomes known. However, this comparing method requires lots of comparing time. And if the spectrum of the unknown stress does not match to any of spectrums of the known stresses in the database, an error occurs. As a complete and continuous database corresponding relationship between stress and spectrum is not available, this measurement method can only deal with the stresses whose values are just equal to the values of the known stresses in database for matching. Once there is a mismatch, the result will lead to erroneous conclusion for there is not known stress for calculating the unknown stress. Increasing the data number of the known stress in the database may improve this dilemma, but it is real not practice.

Further, all the above techniques measure the fringe order or the retardation. All of which are conducted by way of stress-optic law to convert into stress value so that the stress-optic coefficient of the material to be tested should be known. This requirement is not practical in the on-line real-time inspection. In addition to that, the measurement error of the stress-optic coefficient could be accumulated in the calculation of the stress, which ultimately leads to false stress result.

Therefore, it is crucial to design a method and apparatus to directly and quantitatively measure stress and residual stress in a material without first measuring stress-optic coefficient by using fine information of different colors of light and systematically establishing a database between stress and the corresponding spectrum.

SUMMARY OF THE INVENTION

To accomplish the objective of the present invention, it is noted that the apparatus of the present invention is able to quantify the unknown stress and residual stress in the material to be tested. In short, the apparatus is used to quantify the unknown stress and residual stress of a material to be tested.

It is to be noted that the apparatus in accordance with the present invention to quantify the unknown stress and residual stress of a material to be tested includes:

a light source for generating light beam of a single wavelength or multiple wavelengths;

a polarizer in front of the light source for converting a light beam from the light source into a beam with linear polarization;

a first quarter-wave plate in front of the polarizer for generating circular polarization;

a standard material the same as that of the material to be tested and being free of unknown stress and residual stress, which is mounted or located in front of the first quarter-wavelength plate with a face thereof facing a face of the first quarter-wave plate;

a second quarter-wave plate in front of the standard material with its one face facing a face of the standard material;

an analyzer in front of the second quarter-wave plate with its one face facing a face of the second quarter-wave plate;

a loading unit for loading the standard material;

a spectrometer in front of the analyzer for recording intensity of the light passing through the analyzer and obtaining transmissivity spectrum of the standard material under the wavelength of the light source; and a detecting module connected to the spectrometer to have the transmissivity spectrum and consequently a stress quantifying formula for the standard material being formed, which combined with the normalized transmissivity of the material to be tested, a stress distribution of the material to be tested is then obtained.

Still another objective of the present invention is to provide a method for quantifying the unknown stress and residual stress of a material. The method includes the steps of:

loading a standard material;

recording light intensity that passes through the analyzer from the light source to obtain transmissivity spectrum of the standard material under the wavelength of the light source;

repeating the loading step and the recording step to document the change relationship of stress to transmissivity under the influence of a wavelength of a light beam from the light source;

normalizing the change relationship of stress to transmissivity under the influence of a wavelength of a light beam from the light source;

sine fitting the normalized change relationship of the stress to the transmissivity under the influence of a wavelength of a light beam from the light source to obtain the corresponding stress relationship of the normalized transmissivity value under the influence of a wavelength of a light beam from the light source;

obtaining relationship between the corresponding stress of the normalized transmissivity value and the wavelength of the light beam from the light source by linear fitting;

obtaining a first stress quantifying formula through the relationship between the corresponding stress of the normalized transmissivity value and the wavelength of the light beam from the light source by scaling;

obtaining stress distribution of the material to be tested by using the first stress quantifying formula and the wavelength of the light beam from the light source and the corresponding normalized transmissivity value of the wavelength of the material.

Still, another method of the preferred embodiment of the present invention includes the steps of:

loading a standard material;

recording light intensity that passes through the analyzer from the light source to obtain transmissivity spectrum of the standard material under the wavelength of the light source;

repeating the loading step and the recording step to document the change relationship of stress to transmissivity under the influence of a wavelength of a light beam from the light source;

normalizing the change relationship of stress to transmissivity under the influence of a wavelength of a light beam from the light source;

obtaining relationship between the variation of the appearing wavelength of the normalized transmissivity spectrum and the variation of the stress;

choosing a known stress and the wavelength of the normalized transmissivity spectrum corresponding to this known stress via the relationship between the variation of the appearing wavelength of the normalized transmissivity spectrum and the variation of the stress to obtain a second stress quantifying formula; and obtaining stress distribution of the material to be tested by using the second stress quantifying formula of the standard material and the corresponding appearing wavelength of the normalized transmissivity spectrum of the material to be tested.

By way of the above device and method, a systematic relationship between stress and spectrum is established so as to precisely measure the unknown stress and the residual stress of a material.

DETAILED DESCRIPTION OF THE INVENTION

In order to describe details of the preferred embodiment of the present invention, description of the structure, and the application as well as the steps are made with reference to the accompanying drawings. It is learned that after the description, any variation, modification or the like to the structure and the steps of the embodiments of the preferred embodiment of the present invention is easily made available to any person skilled in the art. Thus, the following description is only for illustrative purpose only and does not, in any way, try to limit the scope of the present invention.

Figure 1:
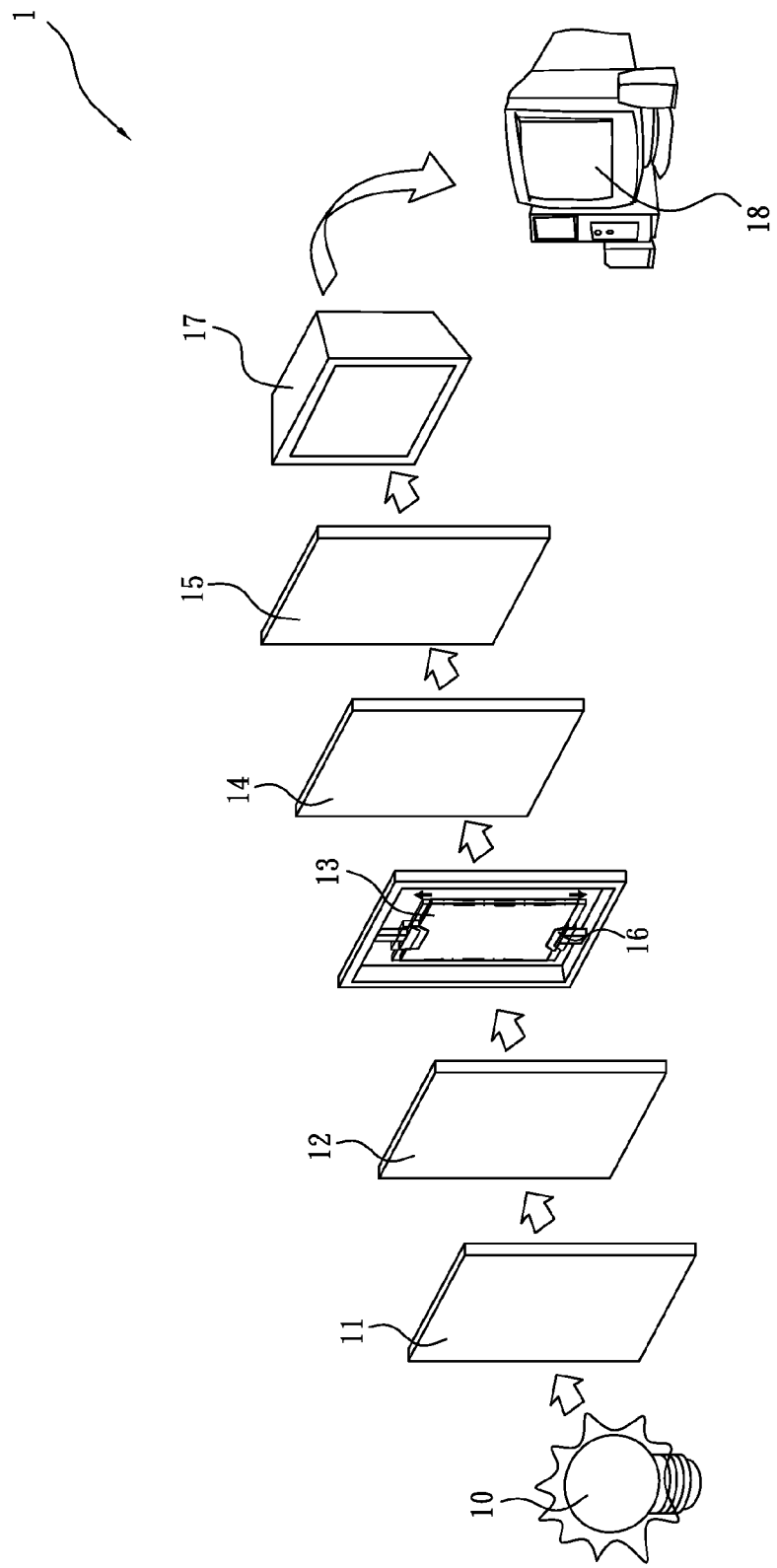
FIG. 1 is an exploded perspective view showing the apparatus used in the preferred embodiment of the present invention.

With reference to FIG. 1, an apparatus used for quantifying unknown stress and residual stress of a material to be tested is shown. The material is a material of birefringence feature or temporary birefringence. The stress quantifying apparatus constructed in accordance with the preferred embodiment of the present invention includes:

a light source 10 for generating a light beam of single wavelength or multiple wavelengths;

a polarizer 11 in front of the light source 10 with a side thereof facing the light source 10 for converting the light beam from the light source 10 into a beam with linear polarization;

a first quarter-wave plate 12 in front of the polarizer 11 with a side thereof facing the light source 10 for generating circular polarization;

a standard material 13 the same as that of the material to be tested and having no unknown stress and residual stress, which is mounted or located in front of the first quarter-wavelength plate 12 with a face thereof facing the other face of the first quarter-wave plate 12;

a second quarter-wave plate 14 in front of the standard material 13 with its one face facing another face of the standard material 13;

an analyzer 15 in front of the second quarter-wave plate 14 with its one face facing another face of the second quarter-wave plate 14;

a loading unit 16 for loading the standard material 13;

a spectrometer 17 in front of the analyzer 15 for recording intensity of the light passing through the analyzer 15 and obtaining transmissivity spectrum of the standard material under the wavelength of the light source; and a detecting module 18 connected to the spectrometer 17 to have the transmissivity spectrum and consequently a stress quantifying formula for the standard material being formed, which combined with the normalized transmissivity of the material to be tested, a stress distribution of the material to be tested is then obtained, in which the light source 10, the polarizer 11, the first quarter-wave plate 12, the standard material 13, the second quarter-wave plate 14 and the analyzer 15 are provided for forming a circular polarization.

The standard material 13 is a glass substrate with temporary birefringence characteristic. In a preferred embodiment of the present invention, the loading unit 16 may be a step motor carrier, a manual carrier, a heating carrier, a humidity carrier or an air pressure carrier. The detecting module 18 may be a general purpose computer.

In a preferred embodiment of the present invention, the detecting module 18 is using loading a standard material 13, recording light intensity that passes through the analyzer 15 from the light source to obtain transmissivity spectrum of the standard material 13 under the wavelength of the light source 10, documenting the change relationship of stress to transmissivity under the wavelength of a light beam from the light source 10, normalizing the change relationship of stress to transmissivity under the wavelength of a light beam from the light source 10, sine fitting the normalized change relationship of the stress to the transmissivity under the wavelength of a light beam from the light source 10 to obtain the corresponding stress relationship of the normalized transmissivity value under the wavelength of a light beam from the light source 10, obtaining relationship between the corresponding stress of the normalized transmissivity value and the wavelength of the light beam from the light source 10 by linear fitting, obtaining the first stress quantifying formula through the relationship between the corresponding stress of the normalized transmissivity value and the wavelength of the light beam from the light source 10, and obtaining stress distribution of the material to be tested by using the first stress quantifying formula and the wavelength of the light beam from the light source 10 and the corresponding normalized transmissivity value of the wavelength of the material.

Still, in another embodiment of the present invention, it is noted that the quantifying method in accordance with the present invention has steps of:

loading a standard material 13, recording light intensity that passes through the analyzer 15 from the light source 10 to obtain transmissivity spectrum of the standard material 13 under the wavelength of the light source 10, repeating the loading step and the recording step to document the change relationship of stress to transmissivity under the wavelength of a light beam from the light source 10, normalizing the change relationship of stress to transmissivity under the wavelength of a light beam from the light source 10, obtaining relationship between the variation of the current wavelength of the normalized transmissivity spectrum and the variation of the stress, choosing a known stress and the appearing wavelength of the normalized transmissivity spectrum corresponding to this known stress via the relationship between the variation of the appearing wavelength of the normalized transmissivity spectrum and the variation of the stress to obtain a second stress quantifying formula and obtaining stress distribution of the material to be tested by using the second stress quantifying formula of the standard material 13 and the corresponding appearing wavelength of the normalized transmissivity spectrum of the material to be tested. The appearing wavelength is the wavelength value corresponding to the peak that is closest to the shortest wavelength of the light source 10 in the normalized transmissivity spectrum. If there is no obvious peak in the normalized transmissivity spectrum, the wavelength value corresponding to the normalized transmissivity of 50% is the appearing wavelength.

In addition, if the normalized transmissivity of the material to be tested is unknown, the standard material 13 is replaced by the material to be tested and the spectrometer 17 is implemented to document the light beam intensity passing through the analyzer 15. Thus the transmissivity spectrum of the material to be tested under the wavelength of the light source 10 is obtained. Consequently, the normalized transmissivity of the material to be tested is obtained.

Figure 2:
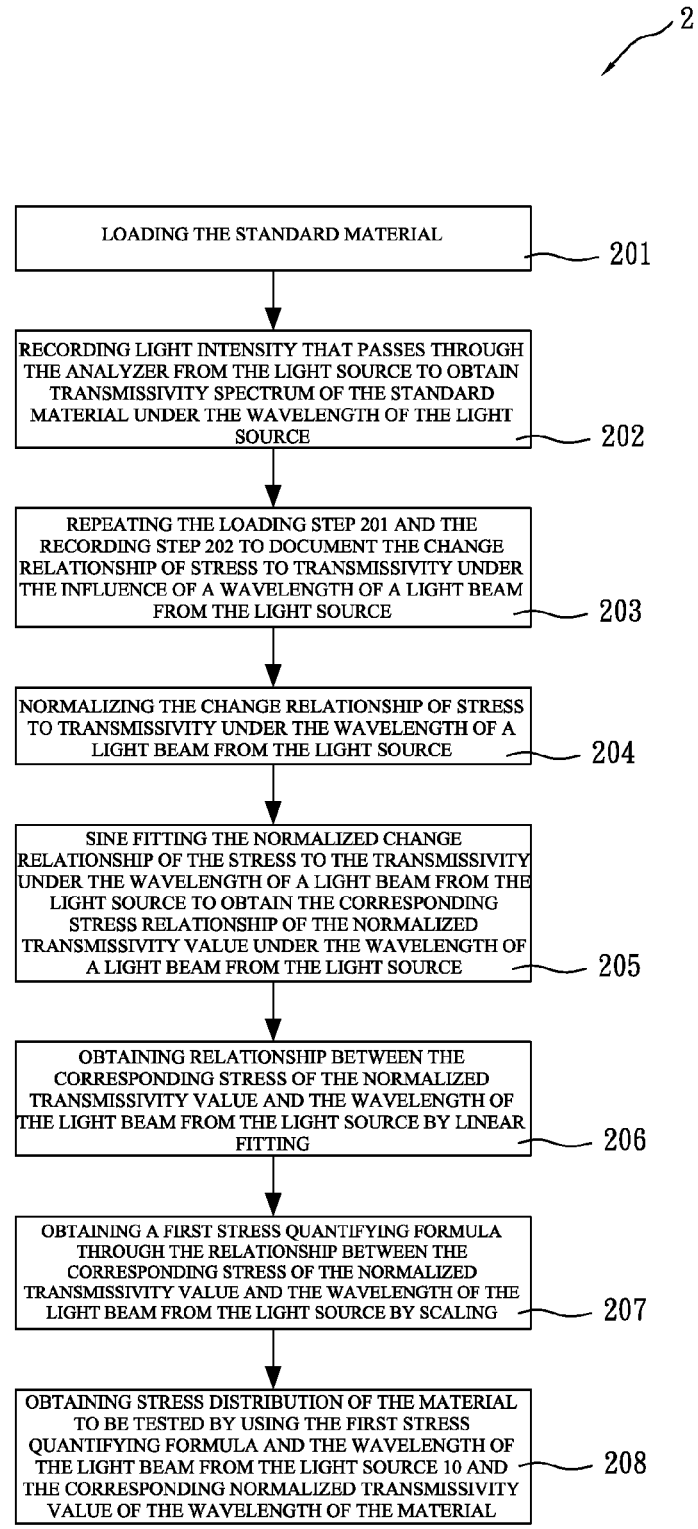
FIG. 2 is a flow chart showing steps of the first preferred embodiment of the present invention.

With reference to FIGS. 1 and 2, the method of the first embodiment 2 of quantifying unknown stress and residual stress of a material implements the apparatus 1 for quantifying the unknown stress and residual stress of a material. The first embodiment of the present invention includes the steps of:

Step 201: loading the standard material 13;

Step 202: recording light intensity that passes through the analyzer 15 from the light source to obtain transmissivity spectrum of the standard material 13 under the wavelength of the light source 10;

Step 203: repeating the loading step 201 and the recording step 202 to document the change relationship of stress to transmissivity under the influence of a wavelength of a light beam from the light source 10;

Step 204: normalizing the change relationship of stress to transmissivity under the wavelength of a light beam from the light source 10;

Step 205: sine fitting the normalized change relationship of the stress to the transmissivity under the wavelength of a light beam from the light source 10 to obtain the corresponding stress relationship of the normalized transmissivity value under the wavelength of a light beam from the light source 10;

Step 206: obtaining relationship between the corresponding stress of the normalized transmissivity value and the wavelength of the light beam from the light source 10 by linear fitting;

Step 207: obtaining a first stress quantifying formula through the relationship between the corresponding stress of the normalized transmissivity value and the wavelength of the light beam from the light source 10 by scaling; and Step 208: obtaining stress distribution of the material to be tested by using the first stress quantifying formula and the wavelength of the light beam from the light source 10 and the corresponding normalized transmissivity value of the wavelength of the material, in which, in step 202, a spectrometer 17 is used to record the light beam intensity passing through the analyzer 15; in step 206, the normalized transmissivity is 100%, 99%, or 50%, however, the percentage is not limited to such results only. After the disclosure of the present invention, the normalized transmissivity percentage can be any number.

In step 208, if the light source 10 is mono-color, the stress distribution of the material to be tested is obtained directly. If the light source 10 is a light source with multiple wavelengths, the detecting module 18 calculates multiple stresses first and then averages the multiple stresses to have the stress distribution of the material to be tested.

Figure 3:
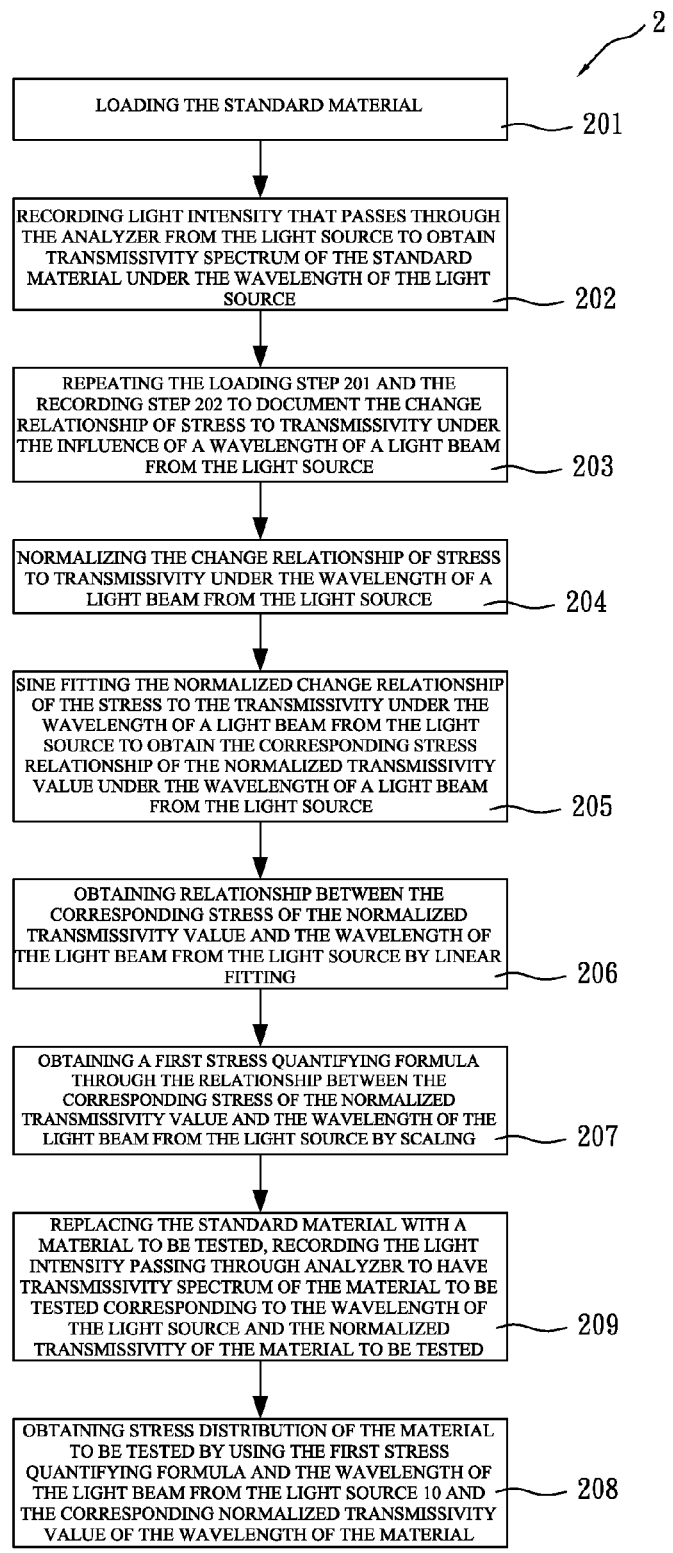
FIG. 3 is a flow chart showing details of the steps shown in FIG. 2.

With reference to FIGS. 1 and 3, if the transmissivity of the material is unknown, then, the method in the first embodiment of the present invention further has a step 209. First of all, the material to be tested is used to replace the standard material 13. The spectrometer 17 is implemented to document the light beam intensity passing through the analyzer 15. Thus the transmissivity spectrum of the material to be tested under the wavelength of the light source 10 is obtained. Consequently, the normalized transmissivity of the material to be tested is obtained. In a preferred embodiment of the present invention, the step 209 is carried out immediately after step 207.

Figure 4:
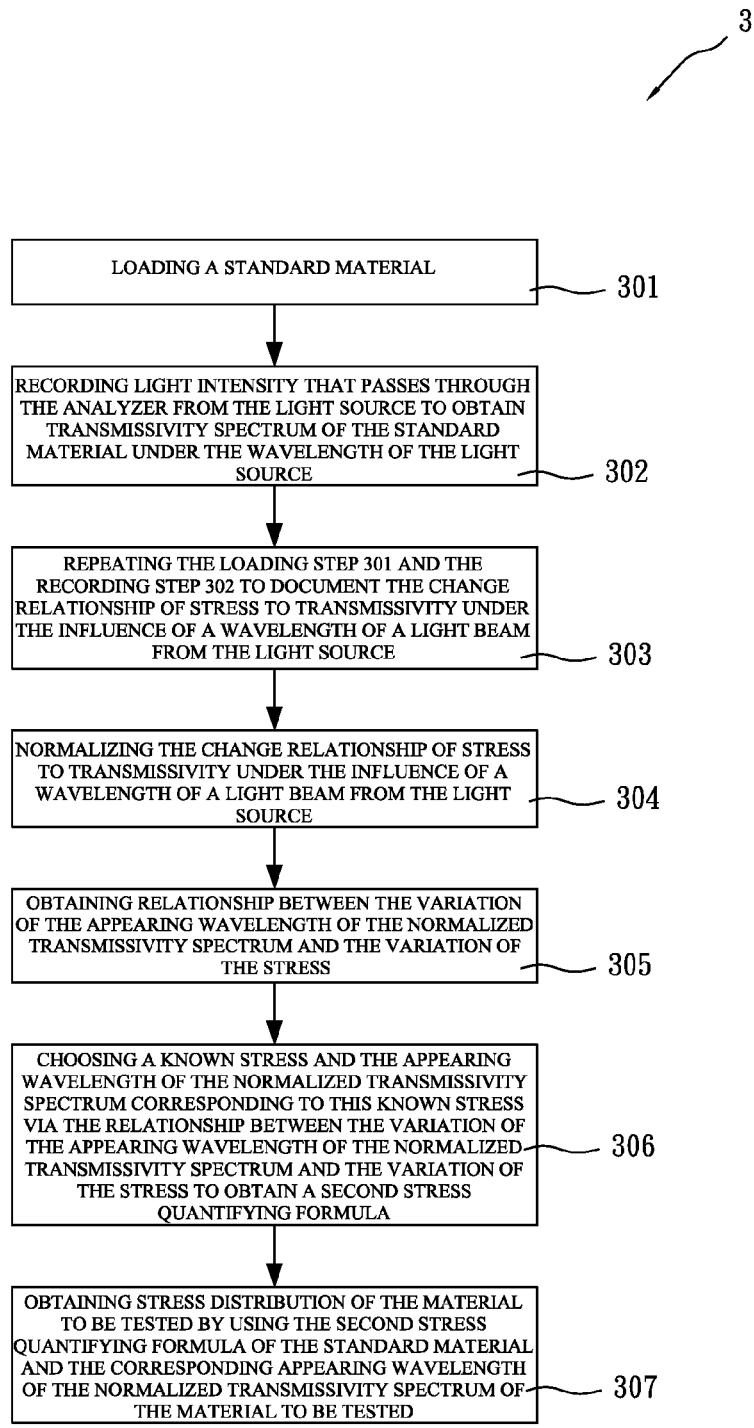
FIG. 4 is a flow chart showing steps of the second preferred embodiment of the present invention.

With reference to FIGS. 1 and 4, the method in the second preferred embodiment 3 of the present invention includes the steps of:

Step 301: loading a standard material 13;

Step 302: recording light intensity that passes through the analyzer 15 from the light source to obtain transmissivity spectrum of the standard material 13 under the wavelength of the light source 10;

Step 303: repeating the loading step 301 and the recording step 302 to document the change relationship of stress to transmissivity under the influence of a wavelength of a light beam from the light source 10;

Step 304: normalizing the change relationship of stress to transmissivity under the influence of a wavelength of a light beam from the light source 10;

Step 305: obtaining relationship between the variation of the appearing wavelength of the normalized transmissivity spectrum and the variation of the stress;

Step 306: choosing a known stress and the appearing wavelength of the normalized transmissivity spectrum corresponding to this known stress via the relationship between the variation of the appearing wavelength of the normalized transmissivity spectrum and the variation of the stress to obtain a second stress quantifying formula; and Step 307: obtaining stress distribution of the material to be tested by using the second stress quantifying formula of the standard material and the corresponding appearing wavelength of the normalized transmissivity spectrum of the material to be tested. The spectrometer 17 is implemented to document the light beam intensity passing through the analyzer 15 in step 302.

Figure 5:
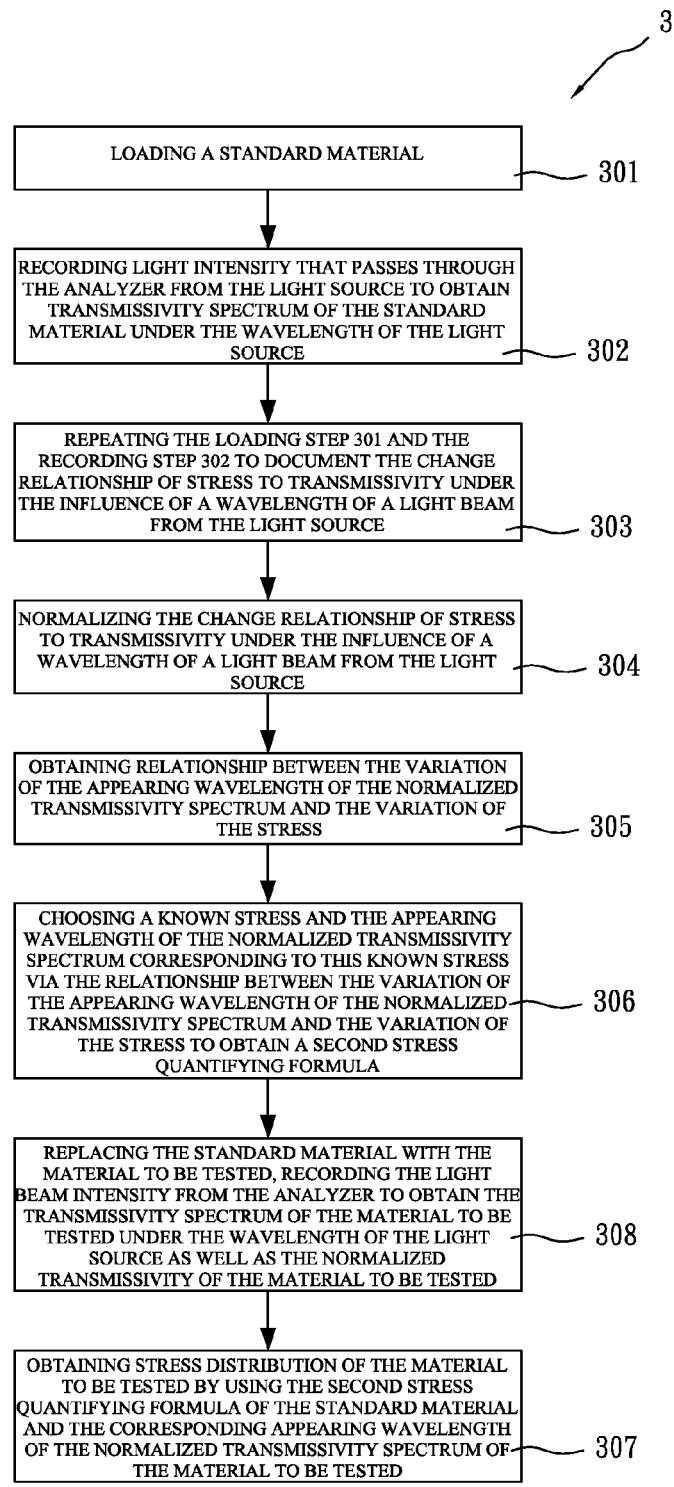
FIG. 5 is a flow chart showing details of the steps shown in FIG. 4.

With reference to FIGS. 1 and 5, if the normalized transmissivity of the material to be tested is unknown, the method of the second preferred embodiment of the present invention further includes steps of:

Step 308: replacing the standard material 13 with the material to be tested, recording the light beam intensity from the analyzer 15 to obtain the transmissivity spectrum of the material to be tested under the wavelength of the light source 10 as well as the normalized transmissivity of the material to be tested. It is preferred that step 308 is carried out right after step 306.

With reference to FIGS. 1, 3, 6A and 9, an example is presented for better understanding the first embodiment of the method of the present invention:

When the apparatus of the present invention is used to measure unknown stress or residual stress of a material to be tested, a standard material 13 the same as that of the material to be tested is placed between the first quarter-wave plate 12 and the second quarter-wave plate 14 and the loading unit 16 is used to carry the standard material 13. After the light source 10 generates a light beam passing through the standard material 13, due to the influence of stress inside the standard material 13, photoelastic effect occurs. The spectrometer 17 is implemented to record the light beam intensity passing through the standard material 13 so that the normalized transmissivity spectrum under the wavelength of the light source 10 of the standard material 13 is obtained.

Figure 6A:
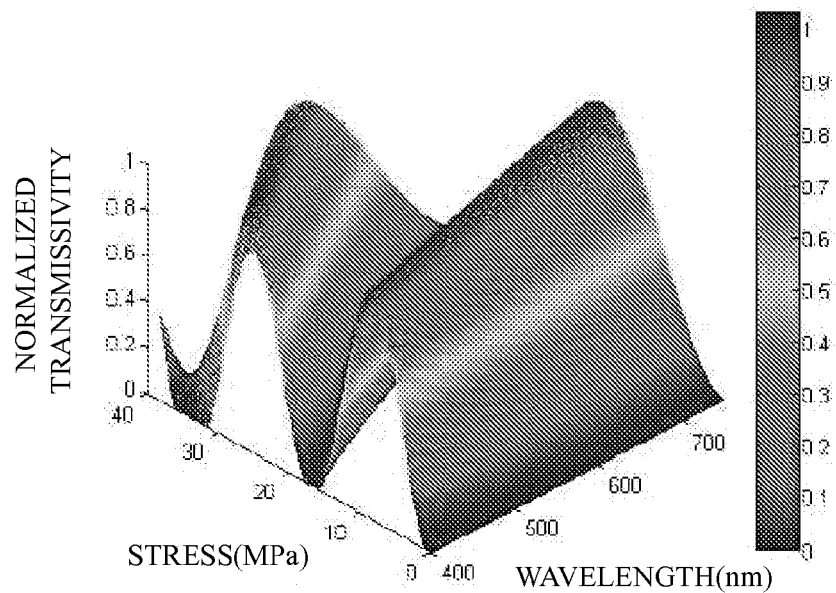
FIG. 6A is a perspective view showing relationship between the corresponding stress of the normalized transmissivity and the wavelength when applying the first method of the present invention.
Figure 6B:
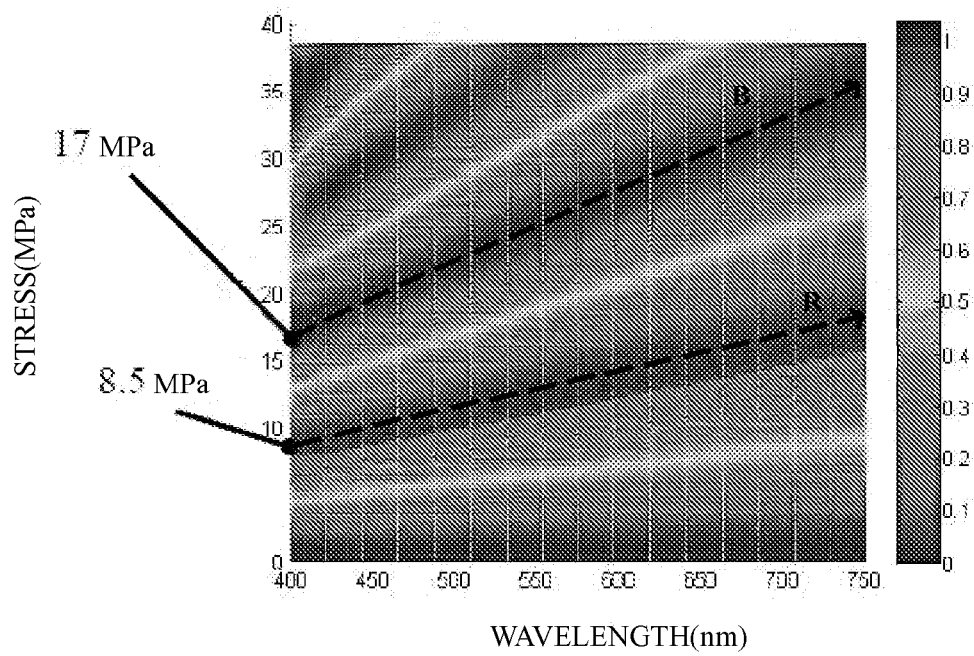
FIG. 6B is a top plan view of FIG. 6A.

With reference to FIG. 6B, it is learned that 400 nanometer, stress 8.5 MPa is used as a start of the dot line R and the dot line R almost passes through the positions where the normalized transmissivity ($T_{n,\lambda}$) is equal to 1, from the normalized transmissivity relation; $T_{n,\lambda}=\sin^2(N\pi)$, the fringe order N is determined to be 0.5. When the wavelength is 400 nanometer and stress is 17 MPa as a start of the dot line B, dot line B almost passes through the positions where the normalized transmissivity is equal to 0 (N=1). It means when a certain stress value is used as a start, the link of all the same normalized transmissivity ($T_n, \lambda$) represents the same fringe order. It is also learned from FIG. 6B that the link of all the same normalized transmissivity ($T_n, \lambda$) is almost like a linear line. Sine fitting the normalized change relationship of the stress to the transmissivity under the wavelength of a light beam from the light source will have the corresponding stress relationship of the normalized transmissivity under the wavelength of the light source. Thus, the values 1, 0.9 and 0.8 of normalized transmissivity under the wavelength of the light source can be taken and presented in FIGS. 7. T(1), T(0.9) and T(0.8) respectively represents the data whose normalized transmissivity value equals to 1, 0.9 and 0.8 under the wavelength of the light source. After linear fitting, the fitting results are well matched with these data, and degrees of correlation are better than 99%. Therefore, it is reasonable to assume the same normalized transmissivity ($T_n, \lambda$) falls on the straight line of stress versus wavelength. Labeling the fitted straight line of the values 1, 0.9 and 0.8 of the normalized transmissivity and the result is shown as the grey straight line.

Figure 7:
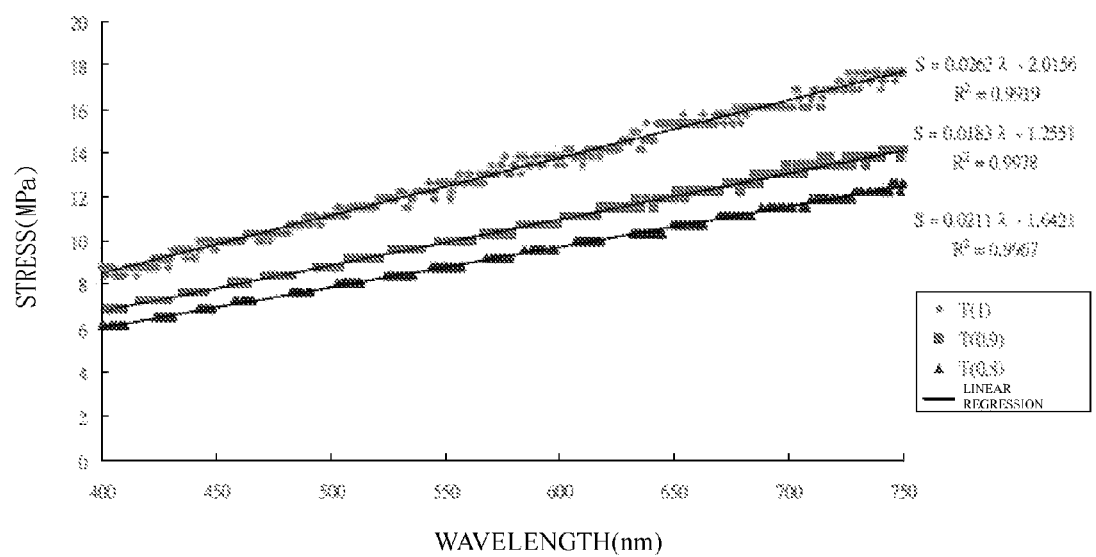
FIG. 7 is a diagram showing relationship between the corresponding stress and the wavelength when the normalized transmissivity is 1; 0.9 and 0.8 used in the first preferred embodiment of the present invention.

It is noted that the position representing normalized transmissivity=1 is the position of half period of the squared sine function. The straight line shown in the grey line in FIG. 7 is drawn by using the normalized transmissivity ($T_n, \lambda$) being equal to 1. Using the normalized transmissivity ($T_n, \lambda$) being equal to 1, the 3-D pattern depicted in FIG. 8 can be represented by equation.

Figure 8:
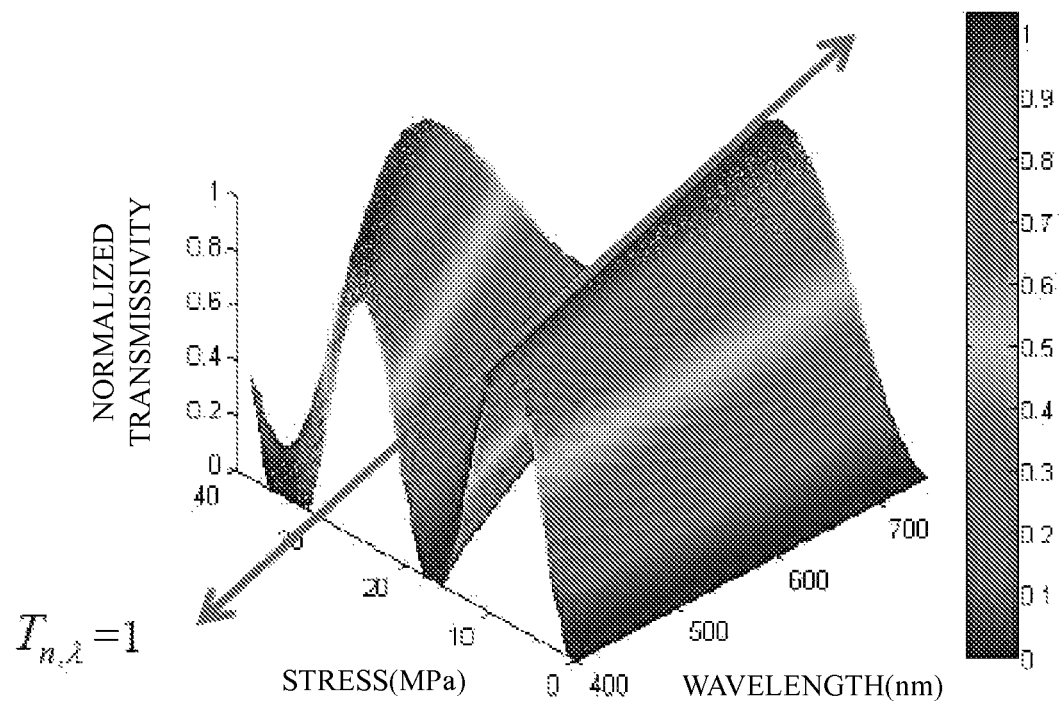
FIG. 8 is a diagram showing the relationship between the corresponding stress and wavelength when the normalized transmissivity equals to 1, which is applied in the first method of the preferred embodiment of the present invention.

In one embodiment of the present invention, it is learned linear function is used to fit the normalized transmissivity ($T_n, \lambda$) being equal to 1 to represent the 3-D pattern in FIG. 8. The normalized transmissivity ($T_n, \lambda$) being equal to 1, as shown in FIG. 7, is shown as a straight line, whose function should be:

$S_\lambda = 0.0236\lambda - 2.0156$, wherein $S_\lambda$, represents the stress when the normalized transmissivity ($T_n, \lambda$) is 1 and the wavelength is $\lambda$.

Figure 9:
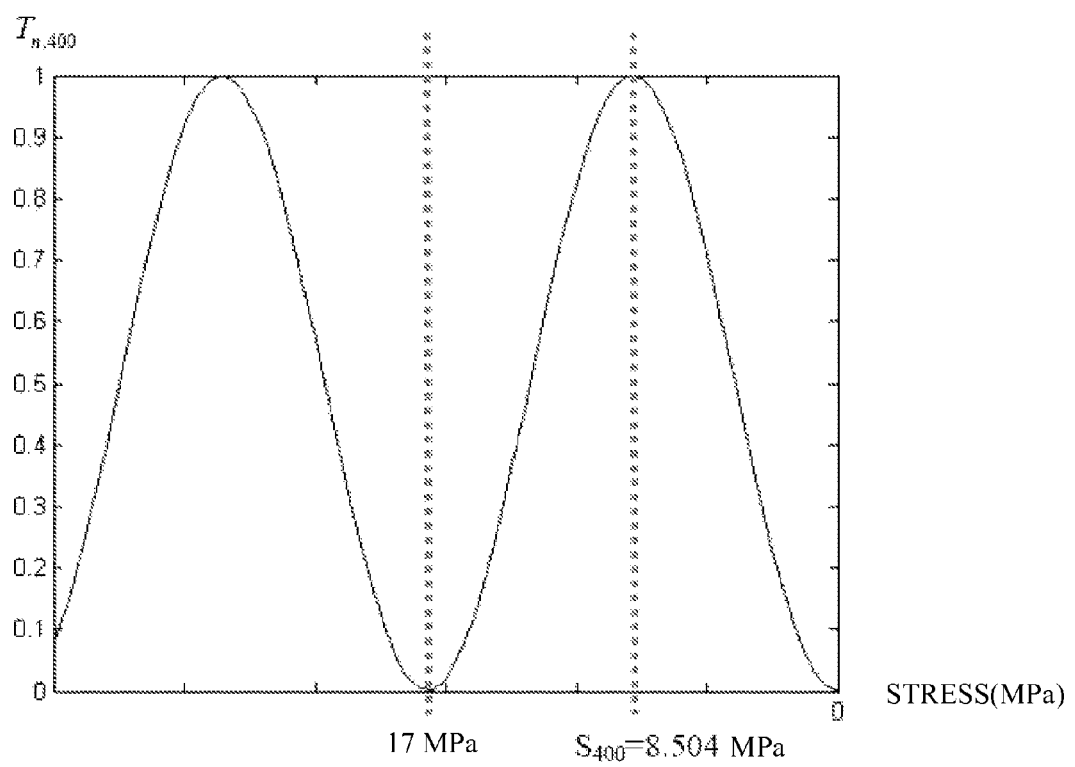
FIG. 9 is a curve diagram showing relationship between the normalized transmissivity and the corresponding stress when the wavelength equals to 400 nanometers.

Taking wavelength=400 nanometer for an example, $S_{400}$ represents the stress when the normalized transmissivity ($T_n$, $\lambda$) is 1 and wavelength is 400 nanometer, which is equal to half cycle of square sine function being equal to 8.504 MPa. As shown in FIG. 9, the square sine function shown by $S_{400}$ is:

$$T_{n,400} = \sin^2\left(\frac{\pi}{2S_{400}}S\right)$$

where S is the stress of the material to be tested

If all the wavelengths are analyzed using the above process, it is learned that the square sine function shown by $S_\lambda$ is:

$$T_{n,\lambda} = \sin^2\left(\frac{\pi}{2S_\lambda}S\right)$$

when the fitted linear function under the condition where the normalized transmissivity is equal to 1 is substituted into the square sine function represented by $S_\lambda$, the result is:

$$T_{n,\lambda} = \sin^2\left[\frac{\pi}{2(0.0263\lambda - 2.0156)}S\right]$$

taking the square root of the normalized transmissivity ($T_n$, $\lambda$) and arc sine the result, the stress (S) of the material to be tested can be represented by the normalized transmissivity ($T_n$, $\lambda$) and the wavelength ($\lambda$) of the light source 10. As a result of this, the first stress formula (F1) for the standard material is:

$$S = \frac{2}{\pi}(0.263\lambda - 2.01560)\sin^{-1}\left(\sqrt{T_{n,\lambda}}\right)$$

If the normalized transmissivity ($T_n$, $\lambda$) under the wavelength of the light source 10 and the wavelength of the light source 10 are known, those information can be substituted into the corresponding normalized transmissivity ($T_n$, $\lambda$) and the wavelength ($\lambda$) to obtain the stress distribution.

Figure 10:
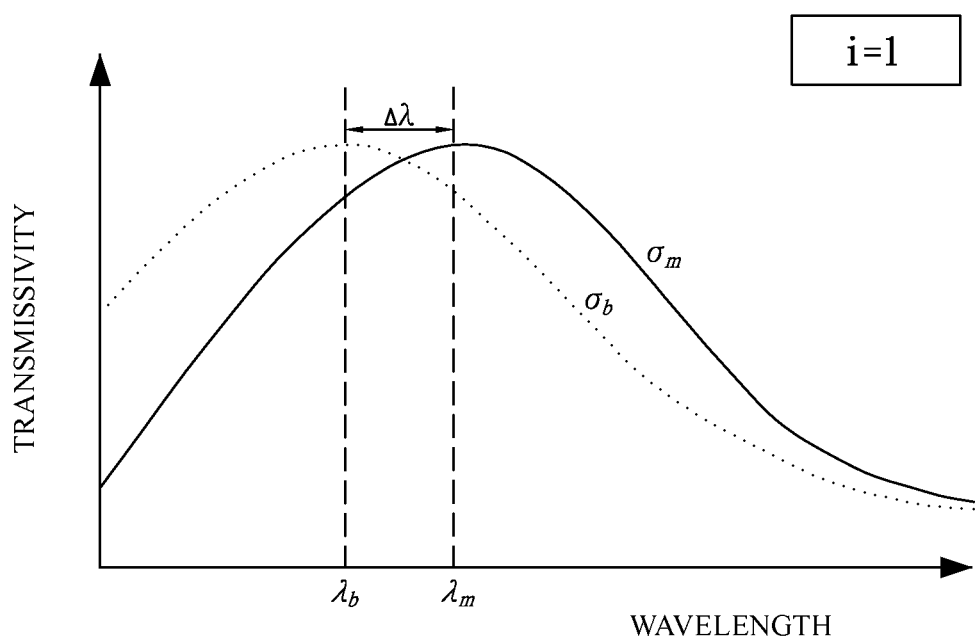
FIG. 10 is diagram showing the curve relationship between the transmissivity and the wavelength applied to the second method of the preferred embodiment of the present invention.

With reference to FIGS. 1, 5 and 10, the second embodiment of the method of the present invention is shown:

When the apparatus constructed in accordance with the present invention is used to measure the unknown and residual stress in a material to be tested, a standard material which is substantially the same as that of the material to be tested is placed between the first quarter-wave plate 12 and the second quarter-wave. The standard material 13 is then placed on the loading unit 16. After the light beam of different wavelengths from the light source 10 is projected onto the material, the resulting fraction from the standard material 13 due to stress in the standard material is sent to the spectrometer 17b for recording and thus the transmissivity spectrum under the wavelength of the light source 10 is obtained. Thereafter, the loading and light intensity recording steps are repeated to record the change relationship between the stress and the transmissivity under the wavelength of the light source 10. A normalized process is conducted to the change relationship between the stress and the transmissivity under the wavelength of the light source 10 to obtain relationship between the appearing wavelength variation of the normalized transmissivity spectrum and the stress variation. The relationship between the appearing wavelength variation of the normalized transmissivity spectrum and the stress variation is used under a known stress to obtain a second stress formula (F2).

In a preferred embodiment of the present invention, the relationship between the current wavelength variation of the normalized transmissivity spectrum and the stress variation is:

$$\Delta\lambda = k_i \cdot \Delta\sigma$$

where $\Delta\lambda$ represents the difference between the appearing wavelengths of two normalized transmissivity spectrums, $\Delta\sigma$ represents the stress difference of the corresponding normalized transmissivity spectrums, $K_i$ represents the coefficients for the relationship between the appearing wavelength variation and the stress variation, metric unit is implemented, i.e. meter/Pascal, i represents the number of peaks existing in the normalized transmissivity spectrum under the corresponding light source 10, thus, $K_i$ can be shown $$K_i = \frac{\sum_{p=1}^{n-1}\left(\frac{\Delta\lambda}{\Delta\sigma}\right)_p}{(n-1)}$$

where n is the total data number of the normalized transmissivity spectrums under peak number i;

p represents two adjacent data of the normalized transmissivity spectrums of $p^{th}$ set.

Therefore, using the relationship between the current wavelength variation of the normalized transmissivity spectrum and the stress variation, the second stress formula ($F_2$) is:

$$\sigma_m = (\lambda_m - \lambda_b)/K_i + \sigma_b$$

where $\sigma_b$ is the known stress;

$\lambda_b$ is the current wavelength of the known stress ($\sigma_b$) corresponding to the normalized transmissivity spectrum.

With reference to FIG. 10, because the corresponding appearing wavelength of the normalized transmissivity spectrum of the material to be tested $\lambda_m$, the coefficient of the relationship between the current wavelength variation of the normalized transmissivity spectrum and the stress variation $K_i$, the known stress $\sigma_b$, and the appearing wavelength $\lambda_b$ of the known stress corresponding to the normalized transmissivity spectrum are all known, the stress distribution of the material to be tested is then obtained.

From the above apparatus and method, it is possible to establish a systematic relationship between the stress and the corresponding spectrum. Unlike the conventional method to compare the similarity between the corresponding spectrums of the stresses, the apparatus as well as the method of the present invention are able to precisely quantify unknown stress or residual stress of a birefringent or temporary birefringent material.

It is also noted that because the design of the telescopic rod 3, the pivotal relationship between the ledge 41 and the foot support 4, as well as the pivotal relationship between the foot support 4 and the telescopic rod 3, the auxiliary device of the present invention is compact and thus small in size for storage.

While the invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

What is claimed is:

1. An apparatus for quantifying unknown stress and residual stress of a material, the material being a birefringent or temporary birefringent material, the apparatus comprising:
 a light source for generating light beam of a single wavelength or multiple wavelengths;
 a polarizer in front of the light source for converting a light beam from the light source into a beam with linear polarization;
 a first quarter-wave plate in front of the polarizer for generating circular polarization;
 a standard material the same as that of the material to be tested and being free of unknown stress and residual stress, which is mounted or located in front of the first quarter-wavelength plate with a face thereof facing a face of the first quarter-wave plate;
 a second quarter-wave plate in front of the standard material with its one face facing a face of the standard material;
 an analyzer in front of the second quarter-wave plate with its one face facing a face of the second quarter-wave plate;
 a loading unit for loading the standard material;
 a spectrometer in front of the analyzer for recording intensity of the light passing through the analyzer and obtaining transmissivity spectrum of the standard material under the wavelength of the light source; and
 a detecting module connected to the spectrometer to have the transmissivity spectrum of the material to be tested and consequently a stress quantifying formula for the standard material, which combined with the normalized transmissivity of the material to be tested, a stress distribution of the material to be tested is then obtained.

2. A method of using an apparatus to quantify unknown and residual stress of a material to be tested, the material being a birefringent or temporary birefringent material, the apparatus comprises a light source, a polarizer, a first quarter-wave plate, a standard material, a second quarter-wave plate, an analyzer, a loading unit, a spectrometer and a detecting module, the light source for generating light beam of a single wavelength or multiple wavelengths, the polarizer in front of the light source for converting a light beam from the light source into a beam with linear polarization, the first quarter-wave plate in front of the polarizer for generating circular polarization, the standard material the same as that of the material to be tested and being free of unknown stress and residual stress, which is mounted or located in front of the first quarter-wavelength plate with a face thereof facing a face of the first quarter-wave plate, the second quarter-wave plate in front of the standard material with its one face facing a face of the standard material, the analyzer in front of the second quarter-wave plate with its one face facing a face of the second quarter-wave plate, the loading unit for loading the standard material, the spectrometer in front of the analyzer for recording intensity of the light passing through the analyzer and obtaining transmissivity spectrum of the standard material under the wavelength of the light source, the detecting module connected to the spectrometer to have the transmissivity spectrum of the material to be tested, the method includes the steps of:
 loading a standard material;
 recording light intensity that passes through the analyzer from the light source to obtain transmissivity spectrum of the standard material under the wavelength of the light source;
 repeating the loading step and the recording step to document the change relationship of stress to transmissivity under the influence of a wavelength of a light beam from the light source;
 normalizing the change relationship of stress to transmissivity under the influence of a wavelength of a light beam from the light source;
 sine fitting the normalized change relationship of the stress to the transmissivity under the influence of a wavelength of a light beam from the light source to obtain the corresponding stress relationship of the normalized transmissivity value under the influence of a wavelength of a light beam from the light source;
 obtaining relationship between the corresponding stress of the normalized transmissivity value and the wavelength of the light beam from the light source by linear fitting;
 obtaining a first stress quantifying formula through the relationship between the corresponding stress of the normalized transmissivity value and the wavelength of the light beam from the light source by scaling;
 obtaining stress distribution of the material to be tested by using the first stress quantifying formula and the wavelength of the light beam from the light source and the corresponding normalized transmissivity value of the wavelength of the material.

3. The method as claimed in claim 2 further comprising a step of replacing the standard material with a material to be tested, recording the light intensity passing through analyzer to have transmissivity spectrum of the material to be tested corresponding to the wavelength of the light source and the normalized transmissivity of the material to be tested.

4. The method as claimed in claim 2, wherein when the light source generates a single color light beam, the stress distribution of the material to be tested is obtained, and
 when the light source generates light beam with multiple wavelengths, the detecting module calculates multiple stresses and averages the multiple stresses to have the stress distribution of the material to be tested.

5. A method of using an apparatus to quantify unknown and residual stress of a material to be tested, the material being a photo-elastic or temporary photo-elastic material, the apparatus comprises a light source, a polarizer, a first quarter-wave plate, a standard material, a second quarter-wave plate, an analyzer, a loading unit, a spectrometer and a detecting module, the light source for generating light beam of a single wavelength or multiple wavelengths, the polarizer in front of the light source for converting a light beam from the light source into a beam with linear polarization, the first quarter-wave plate in front of the polarizer for generating circular polarization, the standard material the same as that of the material to be tested and being free of unknown stress and residual stress, which is mounted or located in front of the first quarter-wavelength plate with a face thereof facing a face of the first quarter-wave plate, the second quarter-wave plate in front of the standard material with its one face facing a face of the standard material, the analyzer in front of the second quarter-wave plate with its one face facing a face of the second quarter-wave plate, the loading unit for loading the standard material, the spectrometer in front of the analyzer for recording intensity of the light passing through the analyzer and obtaining transmissivity spectrum of the standard material under the wavelength of the light source, the detecting module connected to the spectrometer to have the transmissivity spectrum of the material to be tested, the method includes the steps of:

- loading a standard material;
- recording light intensity that passes through the analyzer from the light source to obtain transmissivity spectrum of the standard material under the wavelength of the light source;
- repeating the loading step and the recording step to document the change relationship of stress to transmissivity under the influence of a wavelength of a light beam from the light source;
- normalizing the change relationship of stress to transmissivity under the influence of a wavelength of a light beam from the light source;
- obtaining relationship between the variation of the appearing wavelength of the normalized transmissivity spectrum and the variation of the stress;
- choosing a known stress and the appearing wavelength of the normalized transmissivity spectrum corresponding to this known stress via the relationship between the variation of the appearing wavelength of the normalized transmissivity spectrum and the variation of the stress to obtain a second stress quantifying formula; and
- obtaining stress distribution of the material to be tested by using the second stress quantifying formula of the standard material and the corresponding appearing wavelength of the normalized transmissivity spectrum of the material to be tested.

6. The method as claimed in claim 5 further comprising a step of replacing the standard material with a material to be tested, recording the light intensity passing through analyzer to have transmissivity spectrum of the material to be tested corresponding to the wavelength of the light source and the normalized transmissivity of the material to be tested.

7. The method as claimed in claim 5, wherein when the light source generates light beam with multiple wavelengths, the detecting module calculates the stress distribution of the material to be tested.

* * * * *